United States Patent [19]

Lin et al.

[11] Patent Number: 5,731,461
[45] Date of Patent: Mar. 24, 1998

[54] SURFACTANT COMPOSITION AND PROCESS FOR PRODUCING SAME

[75] Inventors: John Lin, Cedar Park; Upali Weerasooriya, Austin; Paul A. Filler, Leander, all of Tex.

[73] Assignee: Condea Vista Company, Houston, Tex.

[21] Appl. No.: 582,467

[22] Filed: Jan. 3, 1996

[51] Int. Cl.$^6$ .................. C07C 307/02; C07C 311/16
[52] U.S. Cl. .................................................. 564/93
[58] Field of Search .................................... 564/93

[56] References Cited

U.S. PATENT DOCUMENTS

| 5,250,225 | 10/1993 | Oppenlaender et al. | 549/35 |
| 5,298,636 | 3/1994 | Connor et al. | 554/70 |
| 5,380,891 | 1/1995 | Connor et al. | 554/69 |

FOREIGN PATENT DOCUMENTS

| 2127644 | 1/1995 | Canada. |
| WO92/06072 | 4/1992 | WIPO. |
| WO92/06073 | 4/1992 | WIPO. |
| WO92/06701 | 4/1992 | WIPO. |
| WO92/08687 | 5/1992 | WIPO. |
| WO92/03004 | 2/1993 | WIPO. |

OTHER PUBLICATIONS

R.G. Bistline, Jr., et al., "Soap–Based Formulations: VI. Alkylaryl Sulfonamide Derivatives as Lime Soap Dispersing Agents," *JAOCS* 51:126 (1974).

R.G. Bistline, Jr., et al., "Soap–Based Detergent Formulations: XIV. Amphoteric Derivatives of Alkylbenzenesulfonamides". *JAOCS* 53:64 (1976).

W.W. Schmidt, et al., "A Novel Dianionic Surfactant from the Reaction of $C_{14}$–Alkenylsuccinic Anhydride with Sodium Isethionate," *JAOCS*, 71:695 (1994).

A. Patel, et al., "The Phthalation of 2–amino–2–amino–2–deoxy–D–glucose and N–methyl–1–amino–1–deoxy–D–glucitol; Conversion of the Products to Organotin Derivatives. A Ready Migration of Acetyl from Oxygen to Nitrogen Under Neutral Conditions." *Recl. Trav. Chim. Pays–Bas* 107:182 (1988).

*Primary Examiner*—José G. Dees
*Assistant Examiner*—Barbara Badio
*Attorney, Agent, or Firm*—Browning Bushman

[57] ABSTRACT

Disclosed are surfactant compositions comprising a compound of formula I

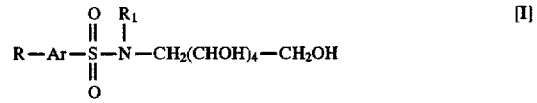

wherein R is an alkyl group having 6 to 20 carbon atoms, $R_1$ is a short chain alkyl group and Ar is an aryl group having 6 carbon atoms.

2 Claims, 1 Drawing Sheet

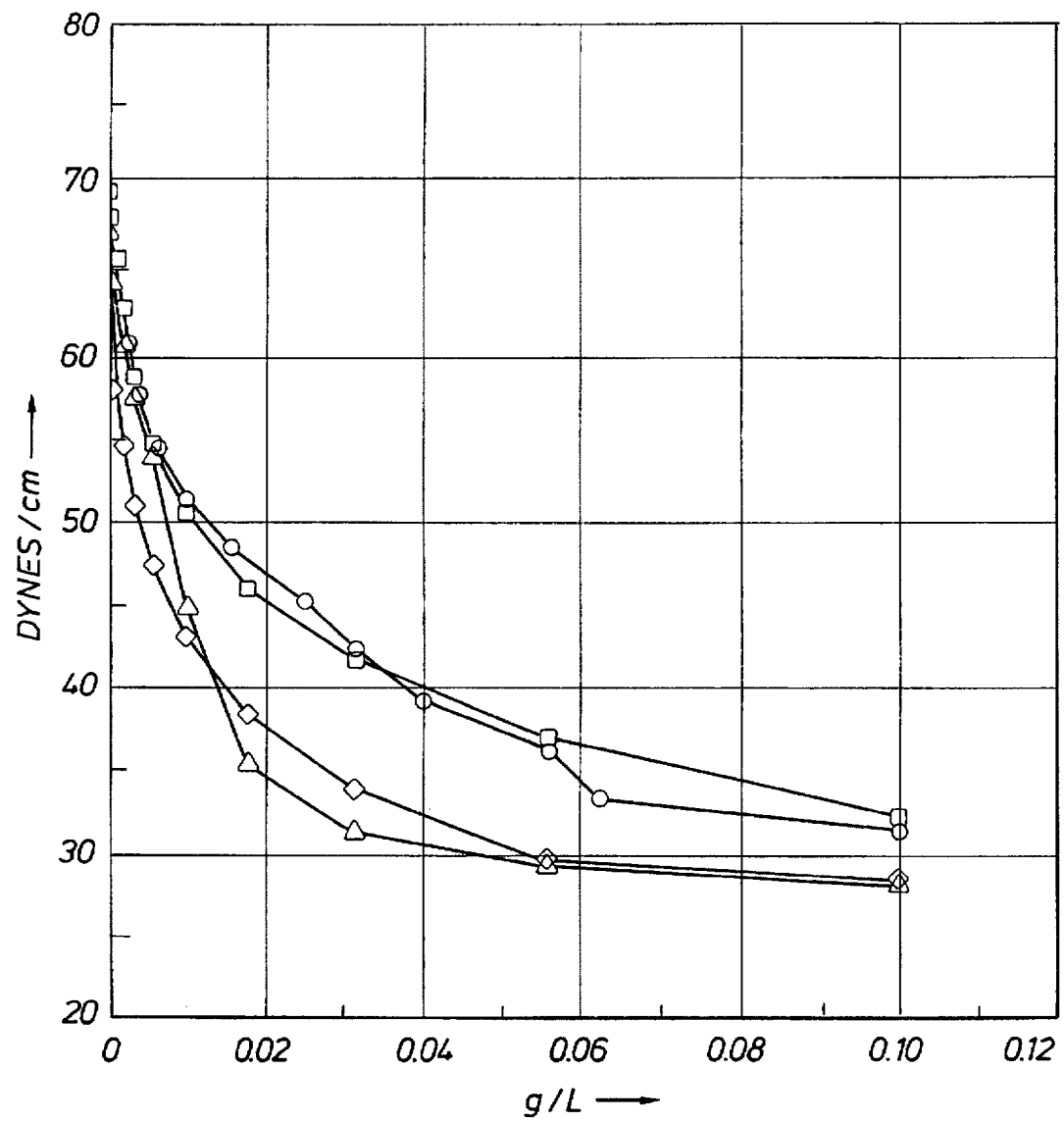

SURFACTANT COMPOSITION AND PROCESS FOR PRODUCING SAME

BACKGROUND OF THE INVENTION

1. Field of the Invention

The present invention relates to a new surfactant or surface active composition and to a process for producing such composition.

2. Description of the Prior Art

It is well known that various derivatives of N-alkylglucamines possess detergency or surfactant properties. U.S. Pat. No. 5,380,891, incorporated herein by reference for all purposes, provides an elaborate background description of various N-alkylglucamine derivatives and methods of producing same for use not only as surfactants but in other applications as well.

In particular, and as disclosed in U.S. Pat. No. 5,380,891, referring to U.S. Pat. No. 2,703,798, one of a series of several possible chemical reactions occasioned by the condensation of N-monoalkylglucamines with fatty acids or oil produces so-call amides, which purportedly possess surfactant or detergency properties.

In an article entitled, "Soap-based Detergent Formulations: XIV. Amphoteric Derivatives of Alkylbenzenesulfonamides," R. G. Bisfline, Jr., et al., AOCS Fall Meeting, Philadelphia, September 1974, there is disclosed the preparation of amphoteric surfactants prepared from alkylbenzenesulfonyl chlorides. In the process disclosed, the alkylbenzenesulfonyl chlorides are reacted with N,N-dimethyl-1,3-diaminopropane or N,N-bis-(2-hydroxyethyl)-1,3-diaminopropane. These products are then quaternized with propanesultone to produce amphoteric surfactants in high yields.

Given the widespread availability of N-alkylglucamines and the fact that they are derived from readily available, renewable natural sources such as glucose or corn syrup, it is clearly desirable to use these compounds as alternatives to petroleum derived compounds in the manufacture of surfactants that can be made into laundry detergents and other cleaning compositions.

SUMMARY OF THE INVENTION

It is therefore an object of the present invention to provide a new surfactant composition.

Another object of the present invention is to provide a surfactant composition derived from N-alkylglucamines.

Yet a further object of the present invention is to provide a process for producing a new surfactant.

Still another object of the present invention is to provide a novel surfactant composition produced from N-alkylglucamines.

The above and other objects of the present invention will become apparent from the description given herein and the appended claims.

In one aspect, the present invention provides a new composition of matter, viz. a nonionic surfactant, having the following general formula:

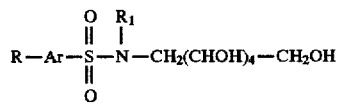

wherein R is an alkyl group having from 6 to 20 carbon atoms, $R_1$ is a short chain alkyl group, and Ar is an aryl group having 6 carbon atoms.

Another aspect of the present invention involves a process for producing the compound shown by Formula I. In the process, an alkyl aromatic compound, e.g., an alkylbenzene, is converted to the corresponding alkylarylsulfonyl chloride either directly or by first converting the alkylbenzene to the corresponding alkylbenzenesulfonic acid which is then reacted with a suitable agent such as thionyl chloride. The alkylarylsulfonyl chloride is then reacted with N-alkylglucamine to produce the composition of Formula I.

BRIEF DESCRIPTION OF THE DRAWINGS

The single FIGURE shows a comparison of the surfactancy properties of the sulfonamide of the present invention with widely used, prior art surfactants.

DESCRIPTION OF THE PREFERRED EMBODIMENTS

The nonionic surfactant of the present invention, which generically is an alkybenzene sulfonamide, has the following general formula:

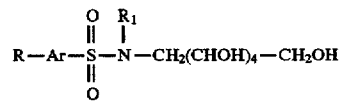

wherein R is an alkyl group having from 6 to 20 carbon atoms, $R_1$ is a short chain alkyl group, and Ar is an aryl group having 6 carbon atoms. Generally speaking, $R_1$ is preferably methyl, ethyl, propyl, butyl, or mixtures thereof. The aryl group will preferably have the formula $C_6H_4$ i.e. it is derived from a benzene nucleus, the group R—Ar— being the residual group of an alkylaromatic starting material.

The process of the present invention provides a novel and convenient way to make nonionic surfactants using linear alkylbenzenes (LABs) and N-alkylglucamines as feedstocks. The alkylbenzenes that can be used in the process of the present invention are represented by the general formula:

$$R-Ar_1 \quad [II]$$

wherein R has the same meaning as described above with respect to Formula I and $Ar_1$ is a phenyl group. Especially preferred are LABs wherein the R group has from about 8 to 18 carbon atoms.

The N-alkylglucamines useful in the practice of the present invention are preferably those derived from D-glucose e.g. N-methyl-D-glucamine. In particular N-alkyl-D-glucamines wherein the alkyl group is short chain e.g. containing from one to four carbon atoms, are preferred. Nonlimiting examples of such N-alkylglucamines N-methylglucamine, N-ethylglucamine, N-propylglucamine, N-butylglucamine and mixtures thereof.

The N-alkylglucamines can be pure or industrial grade. Thus, industrial grade N-alkylglucamines may contain sugars such as glucose, sorbitol or other relatively inert by-products from N-alkylglucamine manufacture, such by-products typically being present in amount of from about 0–5 % by weight.

Preferably the N-alkylglucamines are generally of good color, preferably pure white with no trace of colored impurities and preferably are substantially anhydrous.

The first step in the process of the present invention when starting with a LAB is the conversion of the LAB to the corresponding sulfonyl chloride. This can be accomplished by techniques well known to those skilled in the art, such as, for example, the reaction of the LAB with chlorosulfonic acid ($ClSO_3H$). By way of example, the alkylbenzenesulfonyl chlorides can be produced by the method disclosed by R. G. Bistline, Jr.; W. R. Noble; and W. N. Linfeld, *JAOCS* 51: 126 (1974), incorporated herein by reference for all purposes. In a typical reaction, the LAB is reacted with chlorosulfonic acid in a suitable solvent such as methylene chloride, at, for example, a ratio of 4 equivalents of chlorosulfonic acid to 1 equivalent of LAB. The reaction can be carried out at temperatures from 0° to 50° C., as is well known to those skilled in the art. Once the reaction is complete, the reaction mixture can be added to an ether/aqueous alkali mixture and cooled in a suitable fashion, care being taken to maintain a basic pH. The alkylbenzenesulfonyl chloride migrates to the ether layer, which is separated from the aqueous layer, washed with an aqueous sodium chloride solution and then dried over a suitable drying agent. The ether layer can then be filtered and evaporated under vacuum at low heating, followed by evacuation under high vacuum at room temperature to remove residual solvent, leaving the alkylbenzenesulfonyl chloride.

In an alternate method of producing the alkylarylsulfonyl chloride, the LAB is converted to the corresponding alkylarylsulfonic acid, which can be obtained by ways well known to those skilled in the art as for example, by reacting the LAB with sulfuric acid. The resulting alkylarylsylfonic acid can then be reacted with thionyl chloride to produce the corresponding alkyarylsulfonyl chloride. In this reaction, excess thionyl chloride is generally employed, the mixture being heated from 35° to 90° C. for a suitable period of time to ensure complete reaction. The reaction mixture is then cooled to ambient, excess solvent removed under vacuum with low heating following which the reaction product is subject to high vacuum at room temperature leaving the alkyarylsulfonyl chloride for further use.

To convert the alkylarylsulfonyl chloride into the composition shown in Formula I, the alkylarylsulfonyl chloride is reacted with a desired N-alkylglucamine in a suitable solvent, such as dioxane. In the general procedure, the N-alkylglucamine is added to the solvent with heating at a temperature of from 40° to 110° C. to dissolve the maximum amount of N-alkylglucamine in the solvent. When saturation of the solution has been achieved, the alkylarylsulfonyl chloride is then added, the reaction mixture being stirred and refluxed for a period of time, generally from about 2 to about 6 hours, to complete the condensation of the alkylarylsulfonyl chloride and the N-alkylglucamine. The solvent is then removed in a suitable manner, e.g., by evaporating under reduced pressure, followed by removal of excess N-alkylglucamine and its corresponding hydrochloride. This latter step can be accomplished by taking up the product mixture in ether and filtering off the white solid. The ether layer can then be subjected to multiple washes with dilute hydrochloric acid followed by a dilute sodium bicarbonate wash, following which the ether is dried over magnesium sulfate and filtered. The ether is then removed under reduced pressure, which leaves a product containing a relatively small amount of non-polar by-product. The by-product can be removed by washing with an ether-hexane wash. The remaining material is then placed under high vacuum to obtain the final LAB sulfonamide. Alternatively, the sulfonamide may be isolated from the reaction by-products by recrystallization from a suitable solvent such as butanol.

The invention is more fully demonstrated by the following non-limiting examples:

EXAMPLE 1

Preparation of Alkylarylsulfonyl Chloride from LAB

Into a 100 ml round bottom flask equipped with magnetic stirring, an air condenser, and a drying tube is added 10 g (52.6 mmol) of a $C_8$ LAB and about 25 ml dry methylene chloride. This mixture is stirred at room temperature as four equivalents (14 ml, 210.6 mmol) of chlorosulfonic acid is added in rapid drops. Stirring is maintained for one hour after the addition of the chlorosulfonic acid is complete. The reaction mixture is carefully added to a well-stirred beaker containing ether and aqueous sodium hydroxide cooled in an ice bath. The pH is kept basic by the addition of more aqueous sodium hydroxide as needed. When the entire reaction mixture has been added, the ether layer is recovered using a separatory funnel. This layer is washed once with aqueous sodium chloride and dried over magnesium sulfate. Filtration and evaporation of the ether layer under vacuum with low heating followed by pumping under high vacuum at room temperature to remove residual solvent provided 11.3 g of a hazy light yellow oil.

EXAMPLE 2

Preparation of Alkylarylsulfonyl Chloride from Alkylarylsulfonic Acid

A $C_8$ alkylbenzene sulfonic acid obtained by sulfonating a $C_8$ LAB is reacted with excess thionyl chloride, which is added at room temperature to the sulfonic acid contained in a magnetically stirred round bottom flask equipped with an air condenser and drying tube. The mixture is then refluxed for about 30 minutes. The reaction mixture is then cooled to ambient and the solvent removed under vacuum with low heating on a rotary evaporator followed by high vacuum at room temperature. The resulting alkylbenzenesulfonyl chloride product can be used as is.

EXAMPLE 3

Preparation of LAB Sulfonamide

Into a 500 ml round bottom flask equipped with an air condenser, drying tube and magnetic stirrer, is placed 15.3 g (78.4 mmol) of N-methylglucamine and 300 ml 1,4-dioxane. The mixture is refluxed at a temperature of about 110° C. to dissolve the maximum amount of sugar. When it is evident that solids are no longer dissolving, 11.3 g (39.3 mmol) of a $C_8$ LAB sulfonyl chloride, prepared as per Example 1 or Example 2 above, is added in rapid drops. The reaction mixture is stirred and refluxed for another 4 hours after sulfonyl chloride addition is complete. The dioxane solvent is removed on a rotary evaporator with application of heat. Removal of excess sugar and sugar hydrochloride is accomplished by taking up the product in ether and filtering off the white solid. The ether layer is washed three times with dilute hydrochloric acid followed by a sodium bicarbonate wash. It is then dried over magnesium sulfate and filtered, and the ether is removed under reduced pressure on a rotary evaporator. A small amount of non-polar by-product is removed by washing the product with ether-hexane (1:1 v/v) and discarding the wash. After pumping the gummy product under high vacuum over night, 11.3 g of the $C_8$ LAB sulfonamide is recovered.

NMR analysis on the product establishes that it has the structure as depicted in Formula I.

EXAMPLE 4

Evaluation of Surfactancy of LAB Sulfonamide

The LAB sulfonamide made according to Example 3 was used to make a 1% by weight aqueous solution. The solution exhibited a stable foam and exhibited surfactancy properties comparable to widely used, commercially available surfactants. It was also observed that the sulfonamide performed as a nonionic surfactant and demonstrated synergism when used with an alkylbenzenesulfonic acid sodium salt. As can be seen from the FIGURE, the sulfonamide compares favorably with Alfonic 1012-5, a $C_{10}$–$C_{12}$ alkoxylated alcohol containing about 55–60% ethylene oxide marketed by Vista Chemical Company and Na N-500 L, a $C_{12}$, alkylbenzene sulfonic acid (sodium salt) marketed by Vista Chemical Company. In particular, note that the combination of the sulfonamide and the Na N-500 L in a 1:1 ratio demonstrates synergism.

The foregoing description and examples illustrate selected embodiments of the present invention. In light thereof, variations and modifications will be suggested to one skilled in the art, all of which are in the spirit and purview of this invention.

What is claimed is:

1. A surfactant composition comprising a compound having the general formula:

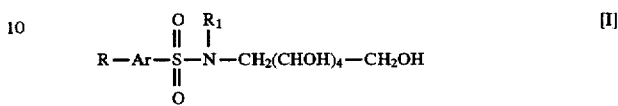

wherein R is an alkyl group having from 6 to 20 carbon atoms, $R_1$ is a short chain alkyl group, and Ar is an aryl group having 6 carbon atoms.

2. The composition of claim 1 wherein $R_1$ is selected from the group consisting of methyl, ethyl, propyl, butyl, and mixtures thereof.

* * * * *